(12) United States Patent
Jacquinot et al.

(10) Patent No.: US 8,153,107 B2
(45) Date of Patent: Apr. 10, 2012

(54) PROCESS FOR THE PREPARATION OF AQUEOUS SUSPENSIONS OF ANIONIC COLLOIDAL SILICA HAVING A NEUTRAL PH AND APPLICATIONS THEREOF

(75) Inventors: Eric Jacquinot, Trosly Breuil (FR); Marie-Laure Perard, Compiegne (FR); Uwe Falk, Bruchköbel (DE); Torsten Henning, Bad Soden (DE)

(73) Assignee: AZ Electronic Materials USA Corp., Somerville, NJ (US)

( * ) Notice: Subject to any disclaimer, the term of this patent is extended or adjusted under 35 U.S.C. 154(b) by 0 days.

(21) Appl. No.: 13/014,207

(22) Filed: Jan. 26, 2011

(65) Prior Publication Data

US 2011/0117035 A1 May 19, 2011

Related U.S. Application Data

(62) Division of application No. 11/872,739, filed on Oct. 16, 2007, now abandoned, which is a division of application No. 10/451,931, filed as application No. PCT/IB02/00038 on Jan. 8, 2002, now Pat. No. 7,629,391.

(30) Foreign Application Priority Data

Jan. 9, 2001 (FR) .................................. 0100219
Oct. 16, 2001 (FR) .................................. 0113328

(51) Int. Cl.
*C01B 33/12* (2006.01)
*C01B 33/20* (2006.01)
*C01B 33/113* (2006.01)
*C01B 33/141* (2006.01)
*A61K 8/00* (2006.01)
*A61K 8/18* (2006.01)
*A61Q 17/04* (2006.01)

(52) U.S. Cl. ................ 424/59; 423/335; 516/79; 516/81

(58) Field of Classification Search .................... 424/59; 516/79, 81; 423/335; 426/11, 16
See application file for complete search history.

(56) References Cited

U.S. PATENT DOCUMENTS 5,196,177 A  3/1993  Watanabe et al.

*Primary Examiner* — Johann Richter
*Assistant Examiner* — Luke Karpinski
(74) *Attorney, Agent, or Firm* — Sangya Jain

(57) ABSTRACT

The instant invention relates to a process for the preparation of an aqueous suspension of anionic colloidal silica having a neutral pH which is stable over time and comprises individualized particles of colloidal silica which are not bound to one another by siloxane bonds. The instant suspensions show high storage stability and are particularly useful for the clarification of beer, for the preparation of cosmetic formulations, for the production of ink for printers, for paints and for anti-corrosive treatments.

20 Claims, No Drawings

PROCESS FOR THE PREPARATION OF AQUEOUS SUSPENSIONS OF ANIONIC COLLOIDAL SILICA HAVING A NEUTRAL PH AND APPLICATIONS THEREOF

CROSS-REFERENCE TO RELATED APPLICATION

This is a divisional of U.S. application Ser. No. 11/872,739, filed Oct. 16, 2007 now abandoned, which is a divisional of U.S. application Ser. No. 10/451,931, filed Jun. 25, 2003 now U.S. Pat. No. 7,629,391, which is the National Stage under 35 U.S.C. 371 of International Patent Application PCT/IB02/00038, filed Jan. 8, 2002, which claims priority from French Patent Application 01 13328, filed Oct. 16, 2001, and French Patent Application 01 00219, filed Jan. 9, 2001, the contents of the foregoing documents incorporated herein by reference in their entirety.

The present invention relates to a process for the preparation of aqueous suspensions of anionic colloidal silica having a neutral pH and the applications thereof.

EP-A-0.878.838 discloses that aqueous suspensions of colloidal silica having a neutral pH may be obtained either by neutralization of alkaline silica sols by an acid solution (solution of nitric, hydrochloric or sulfuric acid), or by neutralization of acid silica sols by a basic solution (solution of potash or ammonia). However, depending on the operating conditions, a limited stability over time of the colloidal suspensions obtained is most often obtained, which limits their commercial development, particularly for colloidal suspensions having a high specific surface, which are the least stable.

The applicant discovered, with surprise, that by mixing an acid silica sol with a basic silica sol, a neutral silica sol was obtained under remarkable conditions and that the sol obtained exhibited remarkable properties, notably a remarkable storage stability over time.

Moreover, by means of the process according to the invention, it is possible to prepare suspensions of anionic colloidal silica having a neutral pH and having a high silica content of at least 5% by weight or even up to 25 to 30% by weight and optionally more than 30% by weight, whilst retaining excellent stability over time, and this in particular for suspensions of individualized particles of colloidal silica not bound to one another by siloxane bonds.

For this reason, the present invention provides a process for the preparation of an aqueous suspension of anionic colloidal silica having a neutral pH (between pH 6 and 8), which is stable over time and comprises individualized particles of colloidal silica which are not bound to one another by siloxane bonds, characterized in that an aqueous suspension of anionic colloidal silica comprising individualized particles of colloidal silica which are not bound to one another by siloxane bonds and having a basic pH is mixed with an aqueous suspension of anionic colloidal silica comprising individualized particles of colloidal silica which are not bound to one another by siloxane bonds and having an acid pH.

The particles of the suspensions of anionic colloidal silica having a neutral pH are preferably individualized particles of colloidal silica which are not bound to one another by siloxane bonds, having advantageously a particle diameter in the range from 4 nm to 150 nm, notably from 4 nm to 100 nm, preferably from 4 nm to 50 nm, particularly from 5 nm to 50 nm and more particularly from 9 nm to 50 nm.

The particles of silica used in the invention advantageously have a specific surface in the range from 20 m$^2$/g to 700 m$^2$/g.

The present invention provides, particularly, a process for the preparation of an aqueous suspension of anionic colloidal silica having a neutral pH (between pH 6 and 8) which is stable over time and comprising individualized particles of colloidal silica which are not bound to one another by siloxane bonds, wherein an aqueous suspension of anionic colloidal silica having a pH in the range from 8.5 to 11, a specific surface in the range from 20 m$^2$/g to 700 m$^2$/g, a particle diameter in the range from 4 nm to 150 nm and having a percentage of silica greater than or equal to 5% by weight, is reacted with an aqueous suspension of anionic colloidal silica having a pH in the range from 2 to 3.5, a specific surface in the range from 20 m$^2$/g to 700 m$^2$/g, a particle diameter in the range from 4 nm to 150 nm, and having a percentage of silica greater than or equal to 5% by weight.

Under preferred conditions of the above process, a suspension of basic anionic colloidal silica containing 5 to 200 parts of silica expressed as dry matter is reacted with an aqueous suspension of acid anionic colloidal silica containing 100 parts of silica expressed as dry matter.

The process according to the present invention makes it possible to prepare aqueous suspensions of colloidal silica having a neutral pH (between pH 6 and 8), a small particle size (between 4 nm and 150 nm) and having a silica concentration of up to 30% by weight.

For this reason, the starting basic and acid suspensions of colloidal silica used for the implementation of the process above contain preferably at least 5%, advantageously at least 10%, notably at least 15%, particularly at least 20% and more particularly at least 30% by weight of silica.

The use of an aqueous suspension of basic colloidal silica instead of a conventional base solution makes it possible to carry out neutralization of an aqueous suspension of acid colloidal silica in a less aggressive and more controlled manner, which is very important during the preparation of neutral aqueous suspensions of colloidal silica on an industrial scale.

The suspensions of anionic silica having a neutral pH as obtained by the process according to the present invention exhibit remarkable properties illustrated below in the experimental part.

Although composed of small particles and therefore having a high specific surface, they exhibit excellent stability over time. However, it is known that without a basic pH, this stability over time of suspensions of colloidal silica is all the more difficult to obtain if the particles of colloidal silica have a high specific surface and therefore a small particle diameter.

Their stability over time is equivalent to that of an aqueous suspension of colloidal silica having a basic pH. This is particularly remarkable.

This stability over time is reflected firstly in a constant viscosity of the aqueous suspension of anionic colloidal silica having a neutral pH during storage, and consequently in the absence of the formation of gels or precipitates over time.

This stability over time is also reflected in a homogeneous density of the anionic colloidal suspension having a neutral pH during storage, that is, absence of settling over time.

These properties render the aqueous suspensions of silica that can be obtained by the process according to the present invention particularly attractive, particularly for the clarification of beer.

For this reason, the present invention also provides the use of aqueous suspensions of neutral colloidal silica described above for the clarification of fermented unfiltered beer and also for the clarification of unfermented unfiltered beer.

More particularly, it provides a process for the clarification of fermented unfiltered beer, characterized in that an aqueous suspension of colloidal silica having a neutral pH as defined above is added to a fermented unfiltered beer, flocculation is allowed to take place, then the deposit formed is separated and a clear beer having good stability and a sodium content equivalent to unrefined beer is obtained.

The present invention also provides a process for the clarification of the beer above, characterized in that an aqueous suspension of colloidal silica having a neutral pH is added to a fermented unfiltered beer as indicated above, in the presence of polyvinyl pyrrolidone.

The present invention also provides a process for the clarification of fermented unfiltered beer above, characterized in that 2 g to 500 g/hectoliter, notably 5 g to 500 g/hectoliter, preferably 20 g to 100 g/hectoliter, more particularly 25 g to 75 g/hectoliter and more specifically 50 g/hectoliter of an aqueous suspension of colloidal silica having a neutral pH above is added to a fermented unfiltered beer.

This suspension was preferably diluted beforehand in 2 to 100 parts of water containing 0.1 g to 10 g of $CO_2$/liter.

The present invention also provides a process for the clarification of fermented unfiltered beer above, characterized in that an aqueous suspension of colloidal silica having a neutral pH according to the invention is added to a fermented unfiltered beer in the presence of 5 g to 50 g/hectoliter, preferably 5 g to 10 g/hectoliter and more specifically about 10 g/hectoliter of polyvinyl pyrrolidone.

Under preferred conditions of implementing the processes above, the aqueous suspension of colloidal silica having a neutral pH is added before the beer is refined.

Under other conditions of use, the suspension of colloidal silica having a neutral pH is added after the beer has been refined and before filtration thereof.

Surprisingly, and unforeseeable by the person skilled in the art, it has now been found that the use of pH-neutral anionic colloidal silicon dioxide gives the preparations very good spreadability on the skin and prevents the sticky feel on the skin which often arises.

A basic prerequisite for the use of this colloidal silicon dioxide in preparations with which humans come into contact is a compatible pH. It has hitherto not been possible to incorporate colloidal silicon dioxide into preparations with a compatible pH since the silicon dioxide precipitates out as a result of neutralization.

Only the possibility of preparing pH-neutral anionic colloidal silicon dioxide makes such preparations possible.

U.S. Pat. No. 5,827,508 describes the use of a dibenzoylmethane sunscreen component together with zinc oxide for protecting against UV radiation. As is described therein, unprotected exposure of human skin to UV radiation can cause short-term negative effects such as erythema (sunburn), and long-term damage such as producing changes in pigmentation and leading to skin cancer.

For this purpose, there is a wide supply of sunscreen preparations for targeted use before and during sunbathing, but, increasingly, also products for daily use against the long-term effects of solar irradiation.

One problem here is the often adequate protection against UVB radiation (290 to 320 nm wavelength) but the inadequate protection against UVA radiation (320 to 400 nm wavelength). The use of dibenzoylmethane sunscreen components, and of other organic UVA filters and/or of inorganic filters such as zinc oxide brings disadvantages in this respect.

A frequent disadvantageous property of sunscreen formulations is poor spreadability on the skin, and a very sticky feel after use.

Finally, the present invention also provides the use of the aqueous suspensions of neutral colloidal silica described above for the preparation of cosmetic creams.

The preparations according to the present invention are suitable for protecting human skin, specifically for protecting against the negative effects of UV radiation. They can be formulated in a broad diversity of product forms, such as, for example, emulsions, gels, fluids, lotions, creams, sprays, sticks, oils, foams, lipsticks, moisture-impregnated cleansing and care wipes etc.

The preferred conditions of implementing the processes according to the invention also apply to the other subject matter of the invention, notably to the applications of the suspensions thus obtained.

The preparations according to the invention comprise between 0.01 and 20% by weight, preferably between 0.1 and 10% by weight, particularly preferably between 0.2 and 7% by weight, of pH-neutral colloidal silicon dioxide in suspension. In order to prevent a whitening effect, the particle size of the silicon dioxide is between 4 nm and 150 nm, preferably between 4 nm and 50 nm.

The preparations according to the invention can comprise one or more further components which can scatter, reflect or absorb UV radiation. The preparation displays a synergistically higher UV absorption than the individual components on their own.

Suitable for this purpose are, inter alia: 2-ethylhexyl p-methoxycinnamate, ethylhexyl salicylate, octocrylene, oxybenzone/benzophenone-3, benzophenone-4, benzophenone-5, ethylhexyl N,N-dimethylaminobenzoate, 4-aminobenzoic acid/PABA, ethylhexyl dimethyl PABA, phenylbenzimidazole-sulphonic acid, homomenthyl salicylate, homosalate, isoamyl methoxy-cinnamate, 4-methylbenzylidenecamphor, 3-benzylidenecamphor, benzene-1,4[bis (3-methylidenecamphor-methylsulphoni-c)]acid, camphor benzalkonium methosulphate, phenylbenzimidazolesulphonic acid, terephthalylidene dicamphorsulphonic acid, butylmethoxydibenzoylmet-hane, benzylidene-camphorsulphonic acid, polyacrylamidomethylbenzylideneca-mphor, PEG-25PABA, ethylhexyltriazone, drometrizole trisiloxane, methylenebis-benzo-triazolyltetramethylbutylphenol, dioctylbutamidotriazone, disodium phenyl dibenzimidazole tetrasulphonate, bis-ethylhexyloxyphenol methoxyphenol-triazine, 4-isopropylbenzyl salicylate, terephthalylidenedicamphorsulphonic acid and mixtures.

Pigments/micropigments which can be of use are surface-treated or untreated titanium dioxide, iron oxide and/or zinc oxide and mixtures thereof.

As further auxiliaries and additives, the preparations according to the invention can comprise self-tanning agents, emulsifiers, thickeners, superfatting agents, fats, waxes, stabilizers, biogenic active ingredients, antioxidants, hydrotropes, solubilizers, bodying agents, surfactants, cationic polymers, glycerol, preservatives, dispersants, and also protein derivatives, such as gelatins, collagen hydrolysates, natural or synthetic-based polypeptides, egg yolk, lecithin, lanolin and lanolin derivates, fatty alcohols, silicones, deodorizing agents, substances with keratolytic and keratoplastic action, enzymes and carrier substances, and moisturizing substances, dyes and fragrances. Furthermore, agents with antimicrobial action can be added to the preparations according to the invention.

Self-tanning agents which can be used are dihydroxyacetones.

Anionic emulsifiers which may be used are: $C_{10}$-$C_{20}$-alkyl and alkylene carboxylates, alkyl ether carboxylates, fatty alcohol sulphates, fatty alcohol ether sulphates, alkylamide sulphates and sulphonates, fatty acid alkylamide polyglycol ether sulphates, alkane sulphates, alkanesulphonates and hydroxyalkanesulphonates, olefinsulphonates, acyl esters of isethionates, sulphofatty acid esters, alkylbenzenesulphonates, alkylphenol glycol ether sulphonates, sulphosuccinates, sulphosuccinic monoesters and diesters, fatty alcohol ether phosphates, protein fatty acid condensation products, alkylmonoglyceride sulphates and sulphonates, alkylglyceride ether sulphonates, fatty acid methyltaurides, fatty acid sarcosinates, sulphoricinoleates, amphoacetates or amphoglycinates, acyl glutamates. These compounds and mixtures thereof are used in the form of their water-soluble or water-dispersible salts, for example the sodium, potassium, magnesium, ammonium, mono-, di- and triethanolammonium salts and analogous alkylammonium salts.

Suitable cationic emulsifiers are quaternary ammonium salts such as di-($C_{10}$-$C_{24}$-alkyl)dimethylammonium chloride or bromide, preferably di-($C_{12}$-$C_{18}$-alkyl)-dimethyl-ammonium chloride or bromide; $C_{10}$-$C_{24}$-alkyldimethylethyl-ammonium chloride or bromide; $C_{10}$-$C_{24}$-alkyltrimethylammonium chloride or bromide, preferably cetyltrimethylammonium chloride or bromide and $C_{20}$-$C_{22}$-alkyltrimethylammonium chloride or bromide; $C_{10}$-$C_{24}$-alkyldimethylbenzyl-ammonium chloride or bromide, preferably $C_{12}$-$C_{18}$-alkyldimethylbenzyl-ammonium chloride; N—($C_{10}$-$C_{18}$-alkyl)-pyridinium chloride or bromide, preferably N—($C_{12}$-$C_{16}$-alkyl)pyridinium chloride or bromide; N—($C_{10}$-$C_{18}$-alkyl)isoquinolinium chloride, bromide or monoalkyl sulphate; N—($C_{12}$-$C_{18}$-alkylpolyoylaminoformylmethyl)pyridinium chloride; N—($C_{12}$-$C_{18}$-alkyl)-N-methylmorpholinium chloride, bromide or monoalkyl sulphate; N—($C_{12}$-$C_{18}$-alkyl)-N-ethylmorphol-inium chloride, bromide or monoalkyl sulphate; $C_{16}$-$C_{18}$-alkylpent-aoxethylammonium chloride diisobutylphenoxyethoxyethyl-dimethylbenzylammon-ium chloride; salts of N,N-diethylaminoethylstearylamide and -oleylamide with hydrochloric acid, acetic acid, lactic acid, citric acid, phosphoric acid, N-acylaminoethyl-N,N-diethyl-N-methylammonium chloride, bromide or monoalkyl sulphate and N-acylaminoethyl-N,N-diethyl-N-benzylammonium chloride, bromide or monoalkyl sulphate, where acyl is preferably stearyl or oleyl.

Examples of suitable nonionic emulsifiers which can be used as hydrophilic component are fatty alcohol ethoxylates (alkylpolyethylene glycols); alkylphenol polyethylene glycols; alkylmercaptan polyethylene glycols; fatty amine ethoxylates (alkylaminopolyethylene glycols); fatty acid ethoxylates (acylpolyethylene glycols); polypropylene glycol ethoxylates (poloxoamers); fatty acid amide polyethylene glycols; N-alkyl-, N-alkoxypolyhydroxy fatty acid amide, in particular fatty acid N-methylglucamides, sucrose esters; polyglycol ethers, alkyl polyglycosides, phosphoric esters (mono-, di- and triphosphoric esters ethoxylated and non-ethoxylated), amine oxides, e.g. $C_{12}$-$C_{18}$-alkyldimethylamine oxide, fatty acid amidoalkyldimethylamine oxide.

Amphoteric emulsifers are: N—($C_{12}$-$C_{18}$-alkyl)-aminopropio-nates and N—($C_{12}$-$C_{18}$-alkyl)-iminodipropionates as alkali metal and mono-, di- and trialkylammonium salts; N-acylaminoalkyl-N, N-dimethylacetobetaine, preferably N—($C_8$-$C_{18}$-acyl)aminopropyl-N—, N-dimethylacetobetaine; $C_{12}$-$C_{18}$-alkyldimethylsulphopropylbetai-ne; amphoteric surfactants based on imidazoline (trade name: Miranol®, Steinapon®), preferably the sodium salt of 1-(carboxymethyloxyethyl)-1-(carboxymethyl)-2-laurylimidazolinium and acyl glutamate.

Suitable non-ionogenic O/W co-emulsifiers are addition products of from 2 to 30 mol of ethylene oxide and/or 0 to 5 mol of propylene oxide with linear fatty alcohols having 8 to 22 carbon atoms, with fatty acids having 12 to 22 C atoms and with alkylphenols having 8 to 15 C atoms in the alkyl group; $C_{12}$-$C_{18}$ fatty acid mono- and diesters of addition products of from 1 to 30 mol of ethylene oxide with glycerol; glycerol mono- and diesters and sorbitan mono- and diesters of saturated and unsaturated fatty acids having 6 to 22 carbon atoms and the ethylene oxide addition products thereof; addition products of from 15 to 60 mol of ethylene oxide with castor oil and/or hydrogenated castor oil; polyol and, in particular, polyglycerol esters, such as, for example, polyglycerol polyricinoleate and polyglycerol poly-12-hydroxystearate. Also suitable are mixtures of compounds from two or more of these classes of substance. The addition products of ethylene oxide and/or propylene oxide with fatty alcohols, fatty acids, alkylphenols, glycerol mono- and diesters, and sorbitan mono- and diesters of fatty acids or with castor oil are known, commercially available products. These are homologue mixtures whose average degree of alkoxylation corresponds to the ratio of the amounts of ethylene oxide and/or propylene oxide and substrate with which the addition reaction is carried out.

Likewise suitable as hydrophilic component are the polymers referred to as "soil release polymers" in particular oligoesters obtained by polycondensation of from 40 to 52, preferably 45 to 50 mol % of one or more dicarboxylic acids or esters thereof, 10 to 40, preferably 20 to 35 mol % of ethylene glycol and/or propylene glycol, 3 to 20, preferably 10 to 15 mol % of polyethylene glycol, 0 to 10 mol % of a water-soluble addition product of from 5 to 80 mol of an alkylene oxide with 1 mol of $C_1$-$C_{24}$-alcohols, $C_6$-$C_{18}$-alkylphenols or $C_8$-$C_{24}$-alkylamines and 0 to 10 mol % of one or more polyols having 3 to 6 hydroxyl groups.

Examples of suitable oily substances are Guerbet alcohols having 6 to 18, preferably 8 to 10 carbon atoms, esters of linear $C_6$-$C_{13}$-fatty acids with linear $C_6$-$C_{20}$-fatty alcohols, esters of branched $C_6$-$C_{13}$-carboxylic acids with linear $C_6$-$C_{20}$-fatty alcohols, esters of linear $C_6$-$C_{18}$-fatty acids with branched alcohols, in particular 2-ethylhexanol, esters of linear and/or branched fatty acids with polyhydric alcohols (such as, for example, dimerdiol or trimerdiol) and/or Guerbet alcohols, triglycerides based on $C_6$-$C_{10}$-fatty acids, vegetable oils, branched primary alcohols, substituted cyclohexanes, Guerbet carbonates, dialkyl ethers, aliphatic or aromatic.

Examples of substances which can be used as superfatting agents are polyethoxylated lanolin derivatives, lecithin derivates, polyol fatty acid esters, monoglycerides and fatty acid alkanolamides, the latter also serving as foam stabilizers. Typical examples of fats are glycerides, and suitable waxes are, inter alia, beeswax, paraffin wax or microcrystalline waxes, optionally in combination with hydrophilic waxes, e.g. cetylstearyl alcohol.

Suitable antioxidants are superoxide dismutase, tocopherol (vitamin E) and ascorbic acid (vitamin C).

Particularly suitable thickeners and dispersants are ethylene glycol esters of fatty acids having 14 to 22, particularly preferably 16 to 22 carbon atoms, in particular mono- and diethylene glycol stearate. Also preferred are stearin monoethanolamide, stearin diethanolamide, stearin isopropanolamide, stearin monoethanolamide stearate, stearyl stearate, cetyl palmitate, glyceryl stearate, stearamide diethanolamide distearate, stearamide monoethanolamide stearate, N,N-dihydrocarbyl ($C_{12}$-$C_{22}$, in particular $C_{16}$-$C_{18}$)-amidobenzoic acid and soluble salts thereof, N,N-di($C_{16}$-$C_{18}$)amidobenzoic acid and derivates. Particularly suitable are polyacrylates, carbomers, in particular water-soluble or water-swellable copolymers based on acrylamidoalkylsulphonic acids and N-vinylcarboxamides.

In principle, suitable solubilizers are all mono- or polyhydric alcohols and ethoxylated alcohols. Preference is given to using alcohols having 1 to 4 carbon atoms, such as ethanol, propanol, isopropanol, n-butanol and isobutanol, glycerol and mixtures of said alcohols. Further preferred alcohols are polyethylene glycols having a relative molecular mass below 2000. Particular preference is given to the use of polyethylene glycol having a relative molecular mass between 200 and 600 and in amounts up to 45% by weight and of polyethylene glycol having a relative molecular mass between 400 and 600 in amounts of from 0.5 to 15% by weight. Further suitable solvents are, for example, triacetin (glycerol triacetate) and 1-methoxy-2-propanol.

Suitable carrier materials are vegetable oils, natural and hydrogenated oils, waxes, fats, water, alcohols, polyols, glycerol, glycerides, liquid paraffins, liquid fatty alcohols, sterol, polyethylene glycols, cellulose and cellulose derivates.

Fungicidal active ingredients which may be used are ketoconazole, oxiconazole, terbinafine, bifonazole, butoconazole, cloconazole, clotrimazole, econazole, enilconazole, fenticonazole, isoconazole, miconazole, sulconazole, tioconazole, fluconazole, itraconazole, terconazole, naftifine, Zn pyrethione and octopirox.

Care substances which can be used are allantoin and bisabolol in the amounts of 0.0001 to 10% by weight.

Suitable cationic polymers are, for example, cationic cellulose derivates, cationic starch, copolymers of diallylammonium salts and acrylamides, quaternized vinylpyrrolidone/vinylimidazole polymers, condensation products of polyglycols and amines, quaternized collagen polypeptides, quaternized wheat polypeptides, polyethyleneimines, cationic silicone polymers such as, for example, amidomethicones, copolymers of adipic acid and dimethylamino-hydroxypropyldiethylenetriami-ne, polyaminopolyamide, cationic chitin derivates such as, for example, chitosan.

Examples of suitable silicone compounds are dimethylpolysiloxane, methylphenylpolysiloxanes, cyclic silicone and amino-, fatty acid-, alcohol-, polyether-, epoxy-, fluorine- and/or alkyl-modified silicone compounds, and polyalkylsiloxanes, polyalkylarylsiloxanes, polyether siloxane copolymers, as described in U.S. Pat. No. 5,104,645 and publications cited therein, which may either be liquid or else in resin form at room temperature.

The preparations according to the invention can be mixed with conventional ceramides, pseudoceramides, fatty acid N-alkylpolyhydroxyalkylamides, cholesterol, cholesterol fatty acid esters, fatty acids, triglycerides, cerebrosides, phospholipids and similar substances.

Examples of available moisturizing substances are isopropyl palmitate, glycerol and/or sorbitol, which can be used in amounts of 0.1 to 50% by weight.

The total amount of auxiliaries and additives can be 1 to 10, preferably 2 to 5% by weight, based on the composition.

Another object of the present invention is the use of the aqueous suspensions of neutral colloidal silica described above for the preparation of ink for ink jet printing.

A further object of the present invention is the use of the aqueous suspensions of neutral colloidal silica described above for paints and anticorrosive treatments.

The examples below illustrate the invention.

EXAMPLE 1

Preparation of an Aqueous Suspension of Colloidal Silica (A) having a pH of 7.0 and a Mean Particle Diameter of 9 nm An aqueous suspension of colloidal silica (B) having a pH of 9, containing 30 wt. % of silica, mean particle diameter 9 nm, and stabilized with sodium was deionised by being passed over a cation exchange resin containing sulfonic groups in the acid form.

An aqueous suspension of colloidal silica (C) having a pH of 2.2 and containing 30 wt. % of silica, mean particle diameter 9 nm, was obtained. This suspension (C) was very unstable and therefore had to be used very quickly.

30.5 g of the aqueous suspension of basic colloidal silica (B) was then added, with stirring, to 145.1 g of the aqueous suspension of acid colloidal silica (C).

The aqueous suspension of neutral colloidal silica (A) obtained had the following characteristics:
pH: 7.0
density: 1.200
% titratable $Na_2O$: 0.095%
% total $Na_2O$: 0.19%
specific surface: 280 $m^2/g$
mean particle diameter: 9 nm
% of silica: 30 wt. %.

The storage stability of this aqueous suspension of neutral colloidal silica (A) was comparable with that of an aqueous suspension of basic colloidal silica of type (B).

| Storage stability | Neutral suspension A | Basic suspension B | Acid suspension C |
|---|---|---|---|
| 25° C. | >6 months | >6 months | 24 hours |
| 50° C. | >6 months | >6 months | 10 hours |
| 75° C. | >6 months | >6 months | 1 hour |

EXAMPLE 2

Preparation of an Aqueous Suspension of Colloidal Silica (D) having a pH of 7.0, Mean Particle Diameter 12 nm An aqueous suspension of colloidal silica (E) having a pH of 9, containing 30 wt. % of silica, mean particle diameter 12 nm, and stabilized with potassium was deionised by being passed over a cation exchange resin containing sulfonic groups in the acid form. An aqueous suspension of colloidal silica (F) having a pH of 2.3 containing 30 wt. % of silica, mean particle diameter 12 nm, was obtained. This suspension (F), which was very unstable, therefore had to be used rapidly.

45 g of the aqueous suspension of basic colloidal silica E were then added, with stirring, to 150 g of the aqueous suspension of acid colloidal silica F. An aqueous suspension of neutral colloidal silica (D) was obtained, the characteristics of which were as follows:
pH: 7.0
density: 1.202
% titratable $K_2O$: 0.3%
specific surface: 200 $m^2/g$
mean particle diameter: 12 nm
% of silica: 30 wt. %.

The storage stability of this aqueous suspension of neutral colloidal silica (D) was tested and it was comparable with the stability of a suspension of basic colloidal silica of type (E).

| Storage stability | Neutral suspension D | Basic suspension E | Acid suspension F |
|---|---|---|---|
| 25° C. | >6 months | >6 months | 8 hours |
| 50° C. | >6 months | >6 months | 1 day |
| 75° C. | >6 months | >6 months | 4 hours |

EXAMPLE 3

Preparation of an Aqueous Suspension of Colloidal Silica (G) having a pH of 7.0. Mean Particle Diameter 25 nm A basic aqueous suspension of colloidal silica (H) having a pH of 9, containing 30 wt. % of silica, mean particle diameter 25 nm, and stabilized with sodium was deionised by being passed over a cation exchange resin containing sulfonic groups in the acid form.

An acid aqueous suspension of colloidal silica (I) having a pH of 2.3 containing 30 wt. % of silica, mean particle diameter 25 nm, was obtained. This suspension (I), which was very unstable, therefore had to be used rapidly.

51 g of the basic aqueous suspension of colloidal silica (H) were then added, with stirring, to 68.5 g of the acid aqueous suspension of colloidal silica (I).

An aqueous suspension of neutral colloidal silica (G) was then obtained, the characteristics of which were as follows:

pH: 7.0 density: 1.197 titratable $Na_2O$: 0.3% specific surface: 115 $m^2/g$ mean particle diameter: 25 nm

% of silica: 30 wt. %.

The storage stability of this suspension of neutral colloidal silica (G) was tested and it was comparable with the stability of a suspension of basic colloidal silica of type (H).

| Storage stability | Neutral suspension G | Basic suspension H |
|---|---|---|
| 25° C. | >6 months | >6 months |
| 50° C. | >6 months | >6 months |
| 75° C. | >6 months | >6 months |

COMPARISON EXAMPLE 1

Preparation of an Aqueous Suspension of Colloidal Silica (A') having a pH of 7, Mean Particle Diameter: 9 nm, Stabilized with Sodium 15 g of 1N sulfuric acid were added, with stirring, to 100 g of the basic aqueous suspension (B) described in Example 1, to obtain a pH of 7.

An aqueous suspension of neutral colloidal silica (A') was obtained, having the following storage stability characteristics:

| Storage stability | Neutral suspension A' | Basic suspension B |
|---|---|---|
| 25° C. | 2 h | >6 months |
| 50° C. | 20 minutes | >6 months |
| 75° C. | rapid gelling | >6 months |

It was observed that the aqueous suspension of neutral colloidal silica (A') obtained by neutralization, by an acid, of an aqueous suspension of basic colloidal silica (B) cannot be used commercially because of its very poor stability.

EXAMPLE 4

Use of the Aqueous Suspension of Neutral Colloidal Silica (A) for Clarification of Fermented Unfiltered Beer 50 g/hectoliter or 100 g/hectoliter of an aqueous suspension of neutral colloidal silica (A) as described in Example 1 were added to unrefined beer (J) which had undergone a principal fermentation of 7 days at 8° C.

This beer, to which the aqueous suspension of neutral colloidal silica (A) had been added, was stored in a tank for 4 weeks at 3° C.

Filtration was then carried out over a kieselguhr filter. The filtered samples were then casked by the brewery to ensure that the influence of oxygen was minimized for the Forcing test.

The stability of the beer was measured by the Forcing test (0° C./40° C./0° C.), the foam was tested by the Ross and Clark test, and the color by the European Brewery Convention test (EBC).

The results obtained are summarized in the table below:

| | Amount of aqueous suspension of neutral colloidal silica (A) added | | |
|---|---|---|---|
| | 0 g/hl | 50 g/hl | 100 g/hl |
| Stability (hot days) | 8 | ≧25 | ≧25 |
| Color (EBC) | 4.4 | 4.4 | 4.4 |
| Foam | 105 | 65 | 55 |
| pH | 4.29 | 4.36 | 4.38 |
| Na in mg/l | 7.9 | 8.3 | 8.1 |
| Ca in mg/l | 29.7 | 30.9 | 29.9 |
| K in mg/l | 460 | 490 | 477 |
| Mg in mg/l | 81.8 | 85.7 | 84.5 |
| Tannoid in mg/l | 55 | 52 | 51 |
| Anthocyanogen in mg/l | 55 | 58 | 55 |
| Flavanoid in mg/l | 40 | 28 | 30 |

It was observed that the addition of 50 g/hl or of 100 g/hl of an aqueous suspension of neutral colloidal silica (A) appreciably improved the stability of the beer without a notable modification in the sodium, calcium, potassium and magnesium contents. Moreover, it was observed that the addition of 50 g/hl or of 100 g/hl of an aqueous suspension of neutral colloidal silica (A) allowed a good reduction in polyphenols (tannoid, anthocyanogen, flavanoid) present in the beer.

An added amount of 50 g/hl of an aqueous suspension of neutral colloidal silica (A) allowed a distinct improvement to be obtained in most of the desired characteristics in comparison with a beer not containing such an aqueous suspension.

EXAMPLE 5

Use of an Aqueous Suspension of Neutral Colloidal Silica in the Presence of Polyvinyl Pyrrolidone for Clarification of Fermented Unfiltered Beer 50 g and 100 g/hectoliter of an aqueous suspension of neutral colloidal silica (A) as described in Example 1 were added to unrefined beer (J) which had undergone a principal fermentation of 7 days at 8° C.

This beer, to which the aqueous suspension of neutral colloidal silica (A) had been added, was stored in a tank for 4 weeks at 3° C.

10 g/hectoliter of polyvinyl pyrrolidone were added, then filtration was carried out over a kieselguhr filter after one hour's contact.

The filtered samples were then casked by the brewery to ensure that the influence of oxygen was minimized for the Forcing test.

The results obtained are summarized in the table below:

|  | 0 g/hl of suspension (A) + 0 g/hl of poly-vinyl pyrrolidone | 50 g/hl of suspension (A) + 10 g/hl of poly-vinyl pyrrolidone | 100 g/hl of suspension (A) + 10 g/hl of poly-vinyl pyrrolidone |
|---|---|---|---|
| Stability (hot days) | 11 | 13 | 15 |
| Color (EBC) | 4.5 | 4.5 | 4 |
| Foam | 110 | 95 | 85 |
| pH | 4.25 | 4.29 | 4.32 |
| Na in mg/l | 7.3 | 7.5 | 7.0 |
| Ca in mg/l | 29.4 | 29 | 29.4 |
| K in mg/l | 456 | 455 | 473 |
| Mg in mg/l | 82.4 | 83.7 | 85 |
| Tannoid in mg/l | 36 | 29 | 30 |
| Anthocyanogen in mg/l | 54 | 46 | 53 |
| Flavanoid in mg/l | 35 | 21 | 31 |

Compared with Example 4, the addition of 10 g/hl of polyvinyl pyrrolidone to 50 or 100 g/hl of the aqueous suspension of neutral colloidal silica A allowed a more pronounced reduction in polyphenols (tannoid, anthocyanogen, flavanoid), and a more stable foam whilst retaining a constant sodium, calcium, potassium and magnesium content.

COMPARISON EXAMPLE 2

Use of an Aqueous Suspension of Basic Colloidal Silica for Clarification of Fermented Unfiltered Beer 25, 50, 75 and 100 g/hectoliter of a suspension of basic colloidal silica (B) as described in Example 1 were added to unrefined beer (K) which had undergone a principal fermentation of 7 days at 8° C.

This beer, to which the aqueous suspension of basic colloidal silica (B) had been added, was stored in a tank for 4 weeks at 3° C.

Filtration was then carried out over a kieselguhr filter. The filtered samples were then casked by the brewery to ensure that the influence of oxygen was minimized for the Forcing test.

The results obtained are summarized in the table below:

|  | 0 g/hl of suspension (B) | 25 g/hl of suspension (B) | 50 g/hl of suspension (B) | 75 g/hl of suspension (B) |
|---|---|---|---|---|
| Stability (hot days) | 0.3 | 2 | 3 | 3.5 |
| Color (EBC) | 2.8 | 1.9 | 1.4 | 1.2 |
| Foam | 107 | 116 | 122 | 118 |
| Na in mg/l | 5.8 | 8.1 | 8.1 | 8.5 |
| Ca in mg/l | 30 | 27 | 27 | 25 |
| Mg in mg/l | 100 | 101 | 95 | 90 |

It was noted that the addition of an aqueous suspension of a basic colloidal silica (B) to the fermented unfiltered beer increased the stability of the latter. On the other hand, a considerable increase in the sodium content of the filtered beer was observed, which is not authorized by the Rheinheitsgebot (German purity law).

EXAMPLE 6

After the principal fermentation of seven days at 8° C., 0 to 100 g/hL of an aqueous suspension of neutral colloidal silica (A) as described in Example 1 were added to unrefined beer (beer originating from the same batch of malt after 7 days' fermentation at 8° C.).

This beer, to which the aqueous suspension of neutral colloidal silica (A) had been added, was stored in a tank for four weeks at 3° C.

Filtration was then carried out over a kieselguhr filter. The filtered samples were then casked by the brewery to ensure that the influence of oxygen was minimized for the Forcing test.

The stability of the beer was measured by means of the Forcing test (0° C./40° C./0° C.). The foam was evaluated by the Ross and Clark test.

The results obtained are summarized in the table below:

| Added amount of aqueous suspension of neutral colloidal silica (A) (g/hL) | Stability (hot days) | Color (EBC*) | Foam | pH |
|---|---|---|---|---|
| 0 | 8 | 4.4 | 105 | 4.29 |
| 10 | >20 | 4.4 | 102 | 4.30 |
| 20 | >20 | 4.4 | 100 | 4.32 |
| 50 | >20 | 4.4 | 65 | 4.36 |
| 100 | >20 | 4.4 | 55 | 4.38 |

*European Brewery Convention

The addition of small quantities of an aqueous suspension of neutral colloidal silica (A) allowed a distinct improvement in the stability of the beer without altering the color and foam values.

EXAMPLE 7

One part of neutral colloidal silica (A) was diluted with 10 parts of carbonated water (0.5 g $CO_2$/L). This dilution had no destabilizing effect on the neutral colloidal silica (A).

After the principal fermentation of seven days at 8° C., 0 to 100 g/hL of colloidal silica were added to unrefined beer (beer originating from the same batch of malt after 7 days' fermentation at 8° C.).

This beer, to which neutral colloidal silica (A) had been added, was stored in a tank for four weeks at 3° C. 10 g of PVPP were then added and, after one hour, filtration was then carried out over a kieselguhr filter. The filtered samples were then casked by the brewery to ensure that the influence of oxygen was minimized for the Forcing test.

The stability of the beer was measured by means of the Forcing test (0° C./40° C./0° C.). The foam was evaluated by the Ross and Clark test.

The results obtained show, as in Example 1, an improvement in the stability whilst retaining a low sodium content and without altering the color, calcium, potassium and magnesium values.

EXAMPLE 8

One part of neutral colloidal silica (A) was diluted with 100 parts of carbonated water (0.5 g $CO_2$/L).

After the principal fermentation of seven days at 8° C., 0 to 100 g/hL of neutral colloidal silica (A) were added to unrefined beer (beer originating from the same batch of malt after 7 days' fermentation at 8° C.).

This beer, to which neutral colloidal silica (A) had been added, was stored in a tank for four weeks at 3° C. 10 g of PVPP were then added and, after one hour, filtration was then carried out over a kieselguhr filter. The filtered samples were then casked by the brewery to ensure that the influence of oxygen was minimized for the Forcing test.

The stability of the beer was measured by means of the Forcing test (0° C./40° C./0° C.). The foam was evaluated by the Ross and Clark test.

The results obtained show, as in Example 1, an improvement in the stability whilst retaining a low sodium content and without altering the color, calcium, potassium and magnesium values.

EXAMPLE 9

Use of an aqueous suspension of neutral colloidal silica for the production of an oil in water sunscreen cream 1) The following constituents were mixed at 80° C.:
   5 parts by weight ®Hostaphat CS120 Clariant (stearyl phosphate)
   2.5 parts by weight ®Tegin M (glyceryl stearate)
   2 parts by weight stearic acid
   1 parts by weight cetyl alcohol
   2 parts by weight Abil 100 (dimethicone)
   3 parts by weight low viscosity mineral oil
   3 parts by weight ®Cetiol 868 (octyl stearate)
   3 parts by weight Myritol 318 (caprylic/capric triglyceride)
   5 parts by weight ®Eusolex 6300 (camphor-4-methylene xylidene)
2) The following were then added:
   0.2 parts by weight ®Pemulen TR1 (crosslinked polymer acrylates/$C_{10-30}$-alkyl acrylate)
   12.5 parts by weight of aqueous suspension of neutral colloidal silica (A)
3) The constituents of part 1) were homogenized in part 2).
4) The following constituents were heated to 80° C.:
   0.6 parts by weight ®Hostapon CL g (sodium lauroyl glutamate)
   4 parts by weight ®Eusolex 232 (phenylbenzimidazone sulfonic acid)
   2.21 parts by weight tromethamine (tris(hydroxymethylol)aminomethane)
   0.2 parts by weight allantoin Clariant
   5 parts by weight glycerol
   preservative: 90 ppm
   Water: 48.49 parts by weight
   Perfume: 0.30 parts by weight
5) Part 4) was introduced into part 3) at 35° C.
6) The emulsion was homogenized.

The sunscreen cream obtained made it possible to avoid the whiteness brought about by titanium dioxide and gave a softer and more pleasant sensation when applied to the skin.

The examples below aim to illustrate the subject-matter of the invention in more detail, without limiting it thereto. In the table, % means % by weight.

EXAMPLE 10

Day Cream with UV Protection

| INCI | Trade name (Example) | % |
|---|---|---|
| Mineral Oil | Paraffin oil low-viscosity | 7 |
| Isopropyl Palmitate | Tegosoft P, Crodamol IPP | 6 |
| Glyceryl Stearate | Tegin M, Cutina GMS | 0.5 |
| Cetearyl Alcohol | Lanette O | 0.5 |
| Capric/Caprylic Triglyceride | Myritol 318 | 2 |
| Benzophenone-3 | Neo Heliopan BB, Eusolex 4360 | 1 |
| Methylene Bis-Benzotriazolyl Tetramethylbutylphenol | Tinosorb M | 3 |
| Silica | neutral Klebosol | 0 to 5 |
| Cetyl Phosphate | Hostaphat CC 100 | 0.5 |
| Caprylyl Methicone | SilCare 41M15 | 1 |
| Ammonium Acryloyldimethyltaurate/VP Copolymer | Aristoflex AVC | 1 |
| Tocopheryl Acetate | Vitamin E acetate | 1 |
| Sodium Cocoyl Glutamate | Hostapon CCG | 1 |
| Water | Water | Ad 100 |
| Glycerol | Glycerol | 5 |
| Citric Acid/Trisodium Citrate | Citric acid/citrate buffer | q.s. |

EXAMPLE 11

Use of an Aqueous Suspension of Neutral Colloidal Silica for the Preparation of Inks for Ink Jet Printing

EXAMPLE 11'

5% of an aqueous suspension of neutral colloidal silica (A) as described in Example 1 was added to a Hostafine Black T ink (80 parts of water/20 parts of diethylene glycol). After mixing, filtration was carried out over a 1 μm filter.

EXAMPLE 11"

2.5% of an aqueous suspension of neutral colloidal silica (A) as described in Example 1 was added to a Duasyn Acid Yellow XX-SF ink (80 parts of water/20 parts of diethylene glycol).

After mixing, filtration was carried out over a 0.45 μm filter.

The physical/chemical characteristics of the inks obtained in Examples 11' and 11" are summarized in the table below.

The printing tests were carried out on a Hewlett Packard 420 printer and evaluated visually:

| | pH | Surface tension (mN/m) | Viscosity (mPas) |
|---|---|---|---|
| Hostafine Black T | 7.7 | 42.0 | 4.337 |
| Hostafine Black T + 5% neutral colloidal silica (A) | 7.8 | 40.6 | 3.294 |
| Duasyn Acid Yellow XX-SF | 4.0 | 62.0 | 2.442 |
| Duasyn Acid Yellow XX-SF + 2.5% neutral colloidal silica (A) | 5.8 | 59.5 | 2.261 |

The addition of small quantities of neutral colloidal silica (A) made it possible to reduce the viscosity, which is advantageous for inks for ink jet printing.

Moreover, the printing obtained with the inks of Examples 11' and 11" was faultless.

The invention claimed is:

1. A process for the preparation of cosmetic creams and for the production of preparations for protecting the human skin against UV radiation, comprising the steps of:

providing an aqueous suspension of anionic colloidal silica having a neutral pH, which is stable over time and comprising individualized particles of colloidal silica which are not bound to one another by siloxane bonds, where said aqueous suspension of anionic colloidal silica comprises individualized particles of colloidal silica which are not bound to one another by siloxane bonds and has a pH in the range from 8.5 to 11, a specific surface in the range from 20 $m^2$/g to 700 $m^2$/g, a mean particle diameter in the range from 4 nm to 150 nm and having a percentage of silica of $\geq 5$ parts by weight, is reacted with an aqueous suspension of anionic colloidal silica comprising individualized particles of colloidal silica which are not bound to one another by siloxane bonds and having a pH in the range from 2 to 3.5, a specific surface in the range from 20 $m^2$/g to 700 $m^2$/g, a mean particle diameter in the range from 4 nm to 150 nm and having a percentage of silica of a 5 parts by weight, further where the mean diameter of the particle is unchanged by the process;

providing a cosmetic cream or a preparation for protecting the human skin against UV radiation: and contacting said aqueous suspension of anionic colloidal silica having a neutral pH with said cosmetic cream or said preparation for protecting the human skin against UV radiation.

2. The process of claim 1, where the aqueous suspension of anionic colloidal silica having a neutral pH is stable for greater than 6 months.

3. The process of claim 1, where the aqueous suspension of anionic colloidal silica has a mean particle diameter in the range from 4 nm to 50 nm.

4. The process of claim 1, where the preparation comprises 0.01 to 20% by weight of the aqueous suspension of anionic colloidal silica having a neutral pH.

5. The process of claim 1, where the preparation comprises 0.1 to 10% by weight of the aqueous suspension of anionic colloidal silica having a neutral pH.

6. The process of claim 1, where the preparation comprises 0.2 to 7% by weight of the aqueous suspension of anionic colloidal silica having a neutral pH.

7. The process of claim 1, where the preparation comprises at least one further component which can scatter, reflect or absorb UV radiation.

8. The process of claim 1, where the preparation comprises at least one further component selected from the group consisting essentially of: 2-ethylhexyl p-methoxycinnamate, ethylhexyl salicylate, octocrylene, oxybenzone/benzophenone-3, benzophenone-4, benzophenone-5, ethylhexyl N,N-dimethylaminobenzoate, 4-aminobenzoic acid/PABA, ethyhexyl dimethyl PABA, phenylbenzimidazolesulphonic acid, homomenthyl salicylate, homosalate, isoamyl methoxycinnamate, 4-methylbenzylidenecamphor, 3-benzylidenecamphor, benzene-1,4[bis(3-methylidenecamphormethylsulphonic)]acid, camphor benzalkonium methosulphate, phenylbenzimidazole-sulphonic acid, terephthalylidene dicamphor-sulphonic acid, butylmethoxydibenzoylmethane, benzylidenecamphorsulphonic acid, polyacrylamidomethylbenzylidenecamphor, PEG-25 PABA, ethylhexyltriazone, drometrizole trisiloxane, methylenebis-benzotriazolyltetramethylbutylphenol, dioctylbutamidotriazone, disodium phenyl dibenzimidazole tetrasulphonate, bisethyihexyloxyphenol methoxyphenoltriazine, 4-isopropylbenzyl salicylate, terephthalylidenedicamphorsulphonic acid, surface-treated or untreated titanium dioxide, surface-treated or untreated iron oxide, surface-treated or untreated zinc oxide and mixtures thereof.

9. The process of claim 1, where the preparation further comprises self-tanning agents.

10. The process of claim 1, where the preparation further comprises pigments.

11. The process of claim 1, where the preparation further comprises emulsifiers.

12. The process of claim 1, where the preparation further comprises super-fatting agents.

13. The process of claim 1, where the preparation further comprises antioxidants.

14. The process of claim 1, where the preparation further comprises biogenic active ingredients.

15. The process of claim 1, where the preparation further comprises preservatives.

16. The process of claim 1, where the preparation further comprises a protein derivative.

17. The process of claim 1, where the preparation further comprises a fatty alcohol.

18. The process of claim 1, where the preparation further comprises an antimicrobial agent.

19. The process of claim 1, where the preparation further comprises a dye.

20. The process of claim 1, where the preparation further comprises polypeptides.

* * * * *